United States Patent [19]

Ronning et al.

[11] Patent Number: 4,556,410

[45] Date of Patent: Dec. 3, 1985

[54] COMPOSITIONS FOR TOBACCO SUCKER GROWTH CONTROL

[75] Inventors: Patricia M. Ronning, St. Paul; Gregg A. Vandesteeg, Roseville, both of Minn.

[73] Assignee: Minnesota Mining and Manufacturing Company, St. Paul, Minn.

[21] Appl. No.: 242,173

[22] Filed: Mar. 10, 1981

[51] Int. Cl.$^4$ ............................................. A01N 25/30
[52] U.S. Cl. ................................. 71/78; 71/DIG. 1; 71/92; 71/103
[58] Field of Search .............................. 71/78, DIG. 1

[56] References Cited

U.S. PATENT DOCUMENTS

| | | | |
|---|---|---|---|
| Re. 30,216 | 2/1980 | Kish | 71/78 |
| 3,100,174 | 8/1963 | Stevens | 424/357 |
| 3,172,816 | 3/1966 | Swintosky | 167/82 |
| 3,326,664 | 6/1967 | Tso | 71/2.6 |
| 3,340,040 | 9/1967 | Tso | 71/78 |
| 3,438,765 | 4/1969 | Tso et al. | 71/78 |
| 3,620,712 | 11/1971 | Conklin | 71/106 |
| 3,894,078 | 7/1975 | Fridinger et al. | 71/103 X |
| 3,900,307 | 8/1975 | Abramitis | 71/78 |
| 3,954,439 | 5/1976 | Papamichael et al. | 71/93 |
| 3,990,884 | 11/1976 | Barker | 71/111 |
| 4,084,956 | 4/1978 | Doyle, Jr. et al. | 71/DIG. 1 X |
| 4,134,754 | 1/1979 | Hoffmann | 71/111 |
| 4,182,621 | 1/1980 | Ogata et al. | 71/78 X |

OTHER PUBLICATIONS

3M Quick Referenced Fact Sheet–Jistar.
Technical Data Bulletin (1980) Mefluidide–Experimental Plant Growth Regulator/Herbicide.
Merk Index, Ninth Edition (1976), p. 584, Entry No. 4345.
Merk Index, Ninth Edition (1976) p. 127, Entry No. 962.
Kirk–Othmer Encyclopedia of Chemical Technology–2nd Edition, vol. 19, p. 542.
Tso et al., "Inhibition of Tobacco Axillary Bud Growth with Fatty Acid Methyl Esters", J. Agr. Food Chem., 13, 78 (1965).

*Primary Examiner*—Catherine L. Mills
*Attorney, Agent, or Firm*—Donald M. Sell; James A. Smith; David R. Cleveland

[57] ABSTRACT

Tobacco desuckering compositions containing mefluidide or maleic hydrazide, and condensate of about 2 to 40 moles of ethylene oxide with one mole of a $C_{12-18}$ unsaturated fatty acid, $C_{12-18}$ unsaturated fatty amine, $C_{12-18}$ unsaturated fatty amide, or $C_{12-18}$ unsaturated fatty alcohol.

16 Claims, No Drawings

COMPOSITIONS FOR TOBACCO SUCKER GROWTH CONTROL

TECHNICAL FIELD

This invention relates to plant growth regulator formulations. In addition, this invention relates to a method for inhibiting the growth of tobacco suckers.

BACKGROUND ART

To stimulate the growth of tobacco leaves, farmers customarily remove the flowers, stem apex, and some top leaves of immature tobacco plants. This process is known as "topping". Topped tobacco plants have a tendency to grow axillary buds ("tobacco suckers") which consume energy otherwise available for the development of tobacco leaves. In order to produce high quality leaves, tobacco plants are desuckered, using manual means or with the aid of plant growth regulation agents. Most tobacco plants in the U.S. are desuckered using maleic hydrazide.

Maleic hydrazide has some undesirable characteristics. Its use can undesirably flavor tobacco leaves, reduce their size, increase their reducing sugar content, imbalance their moisture content, and promote false ripening (premature yellowing) of the leaves. These problems become more severe when maleic hydrazide is applied frequently or at high application rates. for these reasons, it would be very desirable if tobacco desuckering could be carried out using other plant growth regulation agents, or using reduced frequency of application and/or amounts of maleic hydrazide.

Surfactants have long been used to enhance the efficacy of plant growth regulator formulations. Surfactants may provide enhanced penetration, wetting, or sticking characteristics in formulations containing surfactant and plant growth regulator, or assist in dissolving plant growth regulators in carriers such as water or oil. Some surfactants are often themselves plant growth regulation agents which act by contact or systemic action. In general, the mechanism of action of formulations containing surfactants in plants, and the manner of optimizing the choice of surfactant for use with a particular plant species, plant growth regulator, and desired plant growth regulation effect, is not well understood.

A variety of surface-active agents (i.e., surfactants) derived from fatty acids, fatty alcohols, and esters and polyethoxylated condensate products thereof have been used as adjuvants in herbicidal or plant growth regulator formulations. For example, $C_{5-22}$ aliphatic carboxylic acids have been used to increase the solubility of a proton acceptor amino medicament or herbicide in oil in U.S. Pat. No. 3,172,816. Polyunsaturated linoleic or linolenic acids are combined with the grass herbicide "Barban" to combat wild oats in U.S. Pat. No. 4,134,754. Also, $C_{6-18}$ saturated fatty alcohols are combined with isopropyl-N-(3-chlorophenyl)carbamate to provide a composition for inhibiting tobacco sucker development in U.S. Pat. No. 3,438,765. U.S. Pat. No. Re 30216 describes a mixture of $C_{6-18}$ saturated fatty alcohols and maleic hydrazide derivatives for tobacco sucker control, the resulting compositions also optionally containing reaction products of ethylene oxide with saturated long chain fatty acids as surface-active agents. Methyl esters of $C_{6-12}$ saturated fatty acids are mixed with fatty acid esters of polyethoxylated sorbitan (wherein the fatty acid contains about 10 to about 18 carbon atoms and wherein there are about 5 to about 80 ethoxy moieties per molecule) to provide chemical pinching agents in U.S. Pat. No. 3,620,712. Lower alkyl esters of saturated and unsaturated $C_{6-18}$ fatty acids are mixed with isopropyl-N-(3-chlorophenyl)carbamate to provide tobacco desuckering compositions in U.S. Pat. Nos. 3,326,664 and 3,340,040, and are used alone and in combination with isopropyl-N-(3-chlorophenyl)carbamate as tobacco desuckering compositions in Tso et al, "Inhibition of Tobacco Axillary Bud Growth with Fatty Acid Methyl Esters", *J. Agr. Food Chem.*, 13, 78 (1965). Condensates of ethylene oxides and various alcohols have been used in herbicide formulations, for example, in U.S. Pat. Nos. 3,990,884 (lauryl alcohol), 3,954,439 (nonyl phenol), and 4,084,956 (various saturated fatty alcohols, and oleyl alcohol, in combination with the grass herbicide "Barban").

Various surface active agents containing condensates of ethylene oxide and unsaturated fatty acids have been used in non-agricultural applications, for example, as anti-caking agents in cosmetics. Also, polyethoxylated $C_{12-26}$ saturated and unsaturated fatty acid esters have been reported for use as anti-caking and wetting agents in pesticidal formulations containing the non-herbicidally active compound 2-heptadecyl-2-imidazoline, in U.S. Pat. No. 3,100,174.

Despite all of the above reported combinations of herbicides or plant growth regulators (e.g., tobacco desuckering agents) with saturated or unsaturated fatty acids, fatty alcohols, and esters and ethylene oxide condensates thereof, and the above-described combination of the pesticide 2-heptadecyl-2-imidazoline with polyethoxylated unsaturated fatty acid esters, no tobacco desuckering or other plant growth regulation formulations containing condensates of ethylene oxide and unsaturated fatty acids have been previously reported. Also, no tobacco desuckering or other plant growth regulation formulations containing condensates of ethylene oxide and unsaturated fatty amines, unsaturated fatty amides, or unsaturated fatty alcohols have been reported.

DISCLOSURE OF INVENTION

The present invention provides, in one aspect, tobacco desuckering compositions, comprising (a) a plant growth regulation agent selected from 5-acetamido-2,4-dimethyltrifluoromethanesulfonanilide (commonly known as "mefluidide"), 6-hydroxy-3(2H)pyridazinone (commonly known as "maleic hydrazide"), and agriculturally acceptable salts thereof, and (b) surface-active agent, comprising at least one ethoxylated $C_{12-18}$ unsaturated fatty acid, ethoxylated $C_{12-18}$ unsaturated fatty amine, ethoxylated $C_{12-18}$ unsaturated fatty amide, or ethoxylated $C_{12-18}$ unsaturated fatty alcohol, said surface-active agent containing an average of about 2 to 40 oxyethylene radicals per molecule, and preferably an average of about 5 to 10 oxyethylene radicals per molecule. In addition, the present invention provides a method for chemically desuckering tobacco plants, comprising the step of applying to said plants a mixture comprising a suitable diluent, a plant growth regulation agent selected from mefluidide, maleic hydrazide, and agriculturally acceptable salts thereof, and about 0.01 to 5 percent by volume of at least one condensate of about 2 to 40 moles ethylene oxide with one mole of a $C_{12-18}$ unsaturated fatty acid, $C_{12-18}$ unsaturated fatty amine, $C_{12-18}$ unsaturated fatty amide, or $C_{12-18}$ unsaturated fatty alcohol.

DETAILED DESCRIPTION

In the practice of the present invention, the plant growth regulation agents which are used include mefluidide, maleic hydrazide, and agriculturally acceptable salts (e.g., diethanolamine salts) thereof.

The surface-active agents which are used in the present invention are certain ethoxylated unsaturated fatty acids, ethoxylated unsaturated fatty amines, ethoxylated unsaturated fatty amides, or ethoxylated unsaturated fatty alcohols. Ethoxylated unsaturated fatty acids are preferred, and ethoxylated oleates are especially preferred. Suitable unsaturated fatty acids include lauroleic acid, physeteric acid, myristoleic acid, palmitoleic acid, petroselinic acid, petroselaidic acid, oleic acid, elaidic acid, vaccenic acid, ricinoleic acid, linoleic acid, linolelaidic acid, hiragonic acid, alpha or beta eleostearic acid, punicic acid, linolenic acid, elaidolinolenic acid, psuedoeleostearic acid, moroctic acid, alpha or beta parinaric acid, and mixtures thereof. Ethoxylated unsaturated fatty acids for use in this invention can also be prepared from saponified triglycerides of unsaturated fatty acids. Suitable triglycerides of unsaturated fatty acids include triolein, trielaidin, trilinolein, trilinolenin, ricinolein, and mixtures thereof, as well as the mixture of triglycerides obtained from castor oil. Suitable unsaturated fatty amines, amides, and alcohols include the corresponding amines, amides, and alcohols of the above-described unsaturated fatty acids (e.g., oleyl amine, oleyl amide, and oleyl alcohol).

The surface-active agents used in this invention are obtained by reacting each mole of $C_{12-18}$ unsaturated fatty acids, fatty amines, fatty amides, or fatty alcohols with about 2 to 40 moles of ethylene oxide, and preferably about 5 to 10 moles of ethylene oxide, using methods well known in the art.

Surface-active agents which can be used in this invention are readily commercially available and include "Emulphor VN-430", "Emulphor EL-620", "Emulphor EL-719", and "Emulphor ON-870" from GAF, Inc., "Ethofat O/15", "Ethofat O/20", "Ethofat C/15", "Ethofat C/25", "Ethofat 142/20", "Diglycol Oleate L", "Ethomeen O/15", and "Ethomid O/15" from Armak Chemical Co., "Lipal 9C", "Lipal 15C", and "Lipal 25C" from Drew Chemical Corp., "Nopalcol 1-R", "Nopalcol 2-O", and "Nopalcol 6-O" from Nopco Chemical Co., "Neutronyx 330" from Onyx Chemical Co., "Ethosperse OA/2" from Glyco Industries, Inc., "CPH-80-N", "CPH-40-N", "CPH-47-N", "CPH-94-N", and "CPH-81-N" from C. P. Hall Co., "Renex 20", "Brij 92", "Brij 96", and "Brij 98" from ICI, Inc., and "Siponic YX-3", "Siponic YX-5", "Siponic Y-25", and "Siponic Y500-70" from Alcolac Chemical Corp.

The tobacco desuckering compositions of this invention are ordinarily mixed with a suitable diluent, e.g., water, ketones, alcohols, volatile aromatic solvents such as toluene, suitable oils, and other well-known agriculturally acceptable solvents or carriers. Water, 2-octanol, and mixtures thereof are preferred diluents. If desired, a hydrophilic wetting agent can be incorporated into the tobacco desuckering compositions of this invention to assist in wetting of the tobacco plants. For example, alkali salts of alkylaryl sulfonates can be used in water solutions and alkaline earth metal soaps of alkyl aryl sulfonates can be used with emulsifiable concentrates in oil. However, good wetting action is not always necessary to obtain good penetration of the plant growth regulating agent into a tobacco plant using the tobacco desuckering compositions of this invention.

Adjuvants such as anti-caking agents, sticking agents, pigments, fillers, stabilizers, indicators, and the like can also be used if desired. Such adjuvants can be used in amounts typically used in plant growth regulation formulations.

Such factors as tobacco plant species, tobacco plant and/or tobacco sucker maturity, and wind, soil, weather, and water conditions are taken into consideration in determining suitable adjustment of dosage rates and/or number of applications of the compositions of the invention to provide the desired level of tobacco sucker control without waste of the formulation and without harm to the tobacco leaves. Because the efficacy of the compositions of the invention is strongly influenced by the above-mentioned factors and by method of application, only general dosage guidance can be given. However, a suggested dosage rate is about 0.01 percent to 5 percent by volume of final spray of surface-active agent, and about 0.05 kg/hectare to 0.5 kg/hectare of mefluidide or maleic hydrazide. Desired treatment results can generally be obtained at a dosage rate of about 0.1 percent to 2 percent by volume of final spray of surface-active agent.

The compositions of the invention are applied using methods well known in the art. Suitable methods include broadcast or row spraying, dipping, brushing, and the like. Plants should be treated essentially immediately after topping (i.e., on the same day, if possible). Pretreatment with a contact herbicide is generally not necessary. Preferably, treatment is carried out by spraying the leaves to "run-off", that is, until the composition runs from the leaves and collects in the axillary node.

When the compositions of the invention are compared to compositions containing the same amount of plant growth regulation agent but no surface-active agents, the compositions of the invention exhibit improved leaf penetration and decreased leaf wash-off. In addition, the compositions of the invention exhibit increased translocation, i.e., symplastic acropetal and basipetal translocation, within tobacco plants. Such improved penetration and increased translocation can enhance the tobacco desuckering activity of the plant growth regulation agents used in compositions of this invention.

The following examples are offered to aid understanding of the present invention and are not to be construed as limiting the scope thereof.

EXAMPLES 1–11

Plant growth regulation compositions were prepared by combining varying amounts of a commercial solution of maleic hydrazide diethanolamine salt ("MH-30", commercially available from U.S. Rubber Co., containing 0.36 kg/liter active ingredient) and varying amounts of a surface-active agent prepared by combining 15 percent by volume condensate of 5 moles of ethylene oxide per mole of oleic acid (hereafter, the notation "POE(X)" will be used to refer to such condensates where X is the number of moles of ethylene oxide per mole of co-condensate), 15 percent by volume POE(40) ricinoleate, and 70 percent by volume 2-octanol. Each formulation was applied to ten freshly topped and hand-suckered Xanthii variety tobacco plants. The topped plants were in the closed button stage, and nine healthy leaves were left on each topped plant. The compositions were applied by spraying five milliliters of the composition onto the dorsal leaf surface of each plant, using a hand pump sprayer. Control plants were separately treated with compositions containing no maleic hydrazide diethanolamine salt. Four weeks after spraying, any tobacco suckers present on the plants were collected and weighed to provide the total sucker weight per plant.

Shown below in Table I are the amount of maleic hydrazide diethanolamine salt applied to each plant, the concentration by volume of POE(5) oleate plus POE(40) ricinoleate in the final spray, the total collected sucker weight, and the percent of sucker growth supression.

TABLE I

| Example No. | Amt. of regulator per plant, mg | Volume % surface-active agents in final spray | Sucker weight, g | % Sucker growth supression |
|---|---|---|---|---|
| 1 | — | — | 42.03 | — |
| 2 | 10 | — | 18.99 | 55% |
| 3 | 10 | 0.6% | 7.58 | 82% |
| 4 | 15 | — | 11.99 | 71% |
| 5 | 15 | 0.6% | 3.21 | 92% |
| 6 | 20 | — | 11.35 | 73% |
| 7 | 20 | 0.6% | 2.23 | 95% |
| 8 | 25 | — | 7.43 | 82% |
| 9 | 25 | 0.6% | 1.22 | 97% |
| 10 | 50 | — | 1.22 | 97% |
| 11 | 50 | 0.6% | 0.13 | 99.7% |

These examples show that when maleic hydrazide is combined with surface-active agents used in this invention, sucker growth supression is enhanced. For example, application of 15 mg per plant maleic hydrazide diethanolamine salt in a composition containing 0.6 percent by volume of the ethoxylated fatty acide POE(5) oleate and POE(5) ricinoleate gave better sucker control than application of 25 mg per plant of maleic hydrazide diethanolamine salt in a composition which did not contain such ethoxylated fatty acids.

EXAMPLE 12

The method of Examples 1-11 was repeated using 5 mg maleic hydrazide diethanolamine salt per plant. When no ethoxylated fatty acids were added to the composition, 34 percent sucker growth supression was observed. When 1 volume percent POE(5) oleate was added to the composition, 48 percent sucker growth supression was observed.

EXAMPLE 13

The method of Examples 1-12 was repeated using 2 mg maleic hydrazide diethanolamine salt per plant. When no ethoxylated fatty acids were added to the composition, 12 percent sucker growth supression was observed. When 1 volume percent POE(5) oleate was added to the composition, 38 percent sucker growth supression was observed.

EXAMPLES 14-18

The method of Examples 1-13 was repeated, using as plant growth regulator a commercial solution of mefluidide diethanolamine salt ("Mefluidide-2S", commercially available from 3M Co., containing 0.24 kg/liter active ingredient), and using as surface-active agent the POE(5) oleate/POE(40) ricinoleate mixture of Examples 1-11. Shown below in Table II are the amount of mefluidide diethanolamine salt applied to each plant, the concentration by volume of POE(5) oleate plus POE(40) ricinoleate in the final spray, the total collected sucker weight, and the percent of sucker growth supression.

TABLE II

| Example No. | Amt. of regulator per plant, mg | Volume % surface-active agents in final spray | Sucker weight, g | % Sucker growth supression |
|---|---|---|---|---|
| 14 | — | — | 51.62 | — |
| 15 | — | 0.6% | 41.99 | 19% |
| 16 | 20 | 1.4% | 0.78 | 98.5% |
| 17 | 20 | 1.7% | 0.17 | 99.7% |
| 18 | 20 | 2.9% | 0 | 100% |

EXAMPLES 19-23

The method of Examples 1-18 was repeated, using as plant growth regulator a 0.04 kg/liter emulsifiable concentrate of mefluidide free acid in a 15:15:70 volume percent mixture of POE(5) oleate, POE(40) ricinoleate, and 2-octanol. To this emulsifiable concentrate was added varying amounts of POE(5) oleate. Shown below in Table III are the amount of mefluidide free acid applied to each plant, the concentration by volume of POE(5) oleate plus POE(40) ricinoleate in the final spray, the total collected sucker weight, and the percent of sucker growth supression.

TABLE III

| Example No. | Amt. of regulator per plant, mg | Volume % surface-active agents in final spray | Sucker weight, g | % Sucker growth supression |
|---|---|---|---|---|
| 19 | — | — | 71 | — |
| 20 | 2 | — | 66 | 7% |
| 21 | 2 | 1% | 47 | 31% |
| 22 | 5 | — | 72 | 0 |
| 23 | 5 | 1% | 10 | 86% |

Examples 14-23 show that the surface-active agents used in this invention enhance the activity of mefluidide diethanolamine salt and mefluidide free acid as tobacco desuckering agents.

Various modifications and alterations of this invention will be apparent to those skilled in the art without departing from the scope and spirit of this invention and the latter should not be restricted to that set forth herein for illustrative purposes.

What is claimed is:

1. Tobacco desuckering compositions, comprising:
   (a) a plant growth regulation agent selected from 5-acetamido-2,4-dimethyl-trifluoromethanesufanilide, 6-hydroxy-3(2H)pyridazinone, and agriculturally acceptable salts thereof, and
   (b) a surface-active agent, comprising at least one ethoxylated $C_{12-18}$ unsaturated fatty acid, ethoxylated $C_{12-18}$ unsaturated fatty amine, or ethoxylated $C_{12-18}$ unsaturated fatty amide, said surface-active agent containing an average of about 2 to 40 oxyethylene radicals per molecule.

2. Tobacco desuckering compositions according to claim 1, wherein said surface-active agent contains an average of about 5 to 10 oxyethylene radicals per molecule.

3. Tobacco desuckering compositions according to claim 1, further comprising a diluent, and wherein said surface-active agent is about 0.01 to 5 percent by volume of said composition.

4. Tobacco desuckering compositions according to claim 3, wherein said surface-active agent is about 0.1 to 2 percent by volume of said composition.

5. Tobacco desuckering compositions according to claim 1, wherein said surface-active agent is an ethoxylated $C_{12-18}$ unsaturated fatty acid.

6. Tobacco desuckering compositions according to claim 5, wherein said surface-active agent is an oleate.

7. Tobacco desuckering compositions according to claim 6, wherein said surface-active agent contains an average of about 5 to 10 oxyethylene radicals per molecule.

8. Tobacco desuckering compositions according to claim 1, wherein said surface-active agent is an ethoxylated $C_{12-18}$ unsaturated fatty amine.

9. Tobacco desuckering compositions according to claim 1, wherein said surface-active agent is an ethoxylated $C_{12-18}$ unsaturated fatty amide.

10. A method for chemically desuckering tobacco plants, comprising the step of applying to said plants a mixture comprising a suitable diluent, a plant growth regulation agent selected from 5-acetamido-2,4-dimethyltrifluoromethanesulfonanilide, 6-hydroxy-3(2H)pyridazinone, and agriculturally acceptable salts thereof, and about 0.01 to 5 percent by volume of at least one condensate of about 2 to 40 moles ethylene oxide with one mole of a $C_{12-18}$ unsaturated fatty acid, $C_{12-18}$ unsaturated fatty amine, or $C_{12-18}$ unsaturated fatty amide.

11. A method according to claim 10, wherein said mixture contains about 0.1 to 2 percent by volume of said condensate.

12. A method according to claim 11, wherein said mixture contains at least one condensate of about 5 to 10 moles of ethylene oxide with oleic acid.

13. A method according to claim 12, wherein said plant growth regulation agent is 5-acetamido-2,4-dimethyltrifluoromethanesulfonanilide or an agriculturally acceptable salt thereof.

14. A method according to claim 12, wherein said plant growth regulation agent is 6-hydroxy-3(2H)pyridazinone or an agriculturally acceptable salt thereof.

15. Tobacco desuckering compositions according to claim 1, wherein said plant growth regulation agent is 5-acetamido-2,4-dimethyltrifluoromethanesulfonanilide or an agriculturally acceptable salt thereof.

16. Tobacco desuckering compositions according to claim 1, wherein said plant growth regulation agent is 6-hydroxy-3(2H)pyridazinone or an agriculturally acceptable salt thereof.

* * * * *

UNITED STATES PATENT AND TRADEMARK OFFICE
CERTIFICATE OF CORRECTION

PATENT NO. : 4,556,410
DATED : December 3, 1985
INVENTOR(S) : Patricia M. Ronning and Gregg A. Vandesteeg It is certified that error appears in the above-identified patent and that said Letters Patent is hereby corrected as shown below:

Col. 1, line 28, "rates. for" should read
-- rates. For --.

Col. 6, lines 53-54,
"trifluoromethanesufanilide" should read
-- trifluoromethanesulfonanilide --.

Signed and Sealed this

Twenty-fourth Day of June 1986

[SEAL]

Attest:

Attesting Officer

DONALD J. QUIGG

Commissioner of Patents and Trademarks